US011332420B2

(12) United States Patent
Hill, Jr. et al.

(10) Patent No.: US 11,332,420 B2
(45) Date of Patent: May 17, 2022

(54) PROCESSES FOR ISOMERIZING ALPHA OLEFINS (71) Applicant: ExxonMobil Chemical Patents Inc., Baytown, TX (US)

(72) Inventors: Ronald Raymond Hill, Jr., Humble, TX (US); Renyuan Yu, Humble, TX (US); Elizabeth G. Mahoney, Houston, TX (US); Anatoly I. Kramer, Baytown, TX (US); Wenyih F. Lai, Bridgewater, NJ (US); Paul F. Keusenkothen, Houston, TX (US); Nan Hu, Houston, TX (US); Andrew P. Broenen, Houston, TX (US); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/767,829

(22) PCT Filed: Dec. 4, 2018

(86) PCT No.: PCT/US2018/063739
§ 371 (c)(1),
(2) Date: May 28, 2020

(87) PCT Pub. No.: WO2019/118226
PCT Pub. Date: Jun. 20, 2019

(65) Prior Publication Data
US 2020/0369580 A1    Nov. 26, 2020

Related U.S. Application Data (60) Provisional application No. 62/598,596, filed on Dec. 14, 2017.

(51) Int. Cl.
*C07C 5/25* (2006.01)
*B01J 29/70* (2006.01)
*C07C 11/02* (2006.01)

(52) U.S. Cl.
CPC .......... *C07C 5/2518* (2013.01); *B01J 29/7038* (2013.01); *C07C 11/02* (2013.01); *C07C 2529/70* (2013.01)

(58) Field of Classification Search
CPC ..... C07C 11/02; C07C 5/2518; C07C 5/2556; C07C 2529/70
See application file for complete search history.

(56) References Cited

U.S. PATENT DOCUMENTS 2,952,719 A    9/1960  Appell et al.
3,204,009 A    11/1965 Keith et al.
(Continued)

FOREIGN PATENT DOCUMENTS

CN    102649674    8/2012
JP    63196526     8/1988
(Continued)

OTHER PUBLICATIONS

"Distribution of Silicone-to Aluminum Ratios in Zeolite ZSM-5", J. Chem. Soc., FaradayTrans., 1, Jan. 1, 1986, pp. 2645-2649.
(Continued)

*Primary Examiner* — Sharon Pregler
(74) *Attorney, Agent, or Firm* — ExxonMobil Chemical Patents Inc.—Law Department (57) ABSTRACT Processes are described for isomerizing one or more $C_{14}$-$C_{24}$ alpha olefins to produce an isomerization mixture comprising one or more $C_{14}$-$C_{24}$ internal olefins comprising contacting an olefinic feed comprising the one or more $C_{14}$-$C_{24}$ alpha olefins with a catalyst under isomerization conditions, wherein the catalyst comprises a microporous crystalline
(Continued)

aluminosilicate having an MWW framework. The resulting isomerization mixture typically exhibits a low pour point with maintained biodegradability properties as compared to the olefinic feed, and is particularly useful in drilling fluid and paper sizing compositions.

17 Claims, 6 Drawing Sheets

(56) References Cited

U.S. PATENT DOCUMENTS

| | | | |
|---|---|---|---|
| 3,405,196 | A | 10/1968 | Wolff |
| 3,928,485 | A | 12/1975 | Nagase et al. |
| 4,016,245 | A | 4/1977 | Plank et al. |
| 4,076,842 | A | 2/1978 | Plank et al. |
| 4,229,610 | A | 10/1980 | Myers et al. |
| 4,556,477 | A | 12/1985 | Dwyer |
| 4,684,760 | A | 8/1987 | Drake |
| 4,711,873 | A | 12/1987 | Suzukamo et al. |
| 4,749,819 | A | 6/1988 | Hamilton, Jr. |
| 4,822,764 | A | 4/1989 | Suzukamo et al. |
| 4,877,918 | A | 10/1989 | Suzukamo et al. |
| 5,107,047 | A * | 4/1992 | Del Rossi .............. B01J 29/70 585/664 |
| 5,177,281 | A | 1/1993 | Haag et al. |
| 5,194,244 | A | 3/1993 | Brownscombe |
| 5,237,120 | A | 9/1993 | Haag et al. |
| 5,246,566 | A | 9/1993 | Miller |
| 5,252,527 | A | 10/1993 | Zones |
| 5,589,442 | A | 12/1996 | Gee |
| 5,741,759 | A | 4/1998 | Gee et al. |
| 5,965,783 | A | 10/1999 | Gee et al. |
| 6,054,629 | A | 4/2000 | Baralt et al. |
| 7,041,865 | B2 * | 5/2006 | Doll .............. C07C 5/2518 585/664 |
| 7,956,229 | B2 | 6/2011 | Saruwatari et al. |
| 2005/0070747 | A1 | 3/2005 | Brown et al. |
| 2006/0293549 | A1 | 12/2006 | Sigl et al. |
| 2009/0153757 | A1 * | 6/2009 | Nose .............. G09G 3/3629 349/35 |
| 2009/0163757 | A1 | 6/2009 | Gee |
| 2015/0322365 | A1 | 11/2015 | Jeon et al. |

FOREIGN PATENT DOCUMENTS

| | | |
|---|---|---|
| JP | 63196527 | 8/1988 |
| JP | 8040944 | 2/1996 |
| NL | 7209849 | 10/1972 |
| WO | 1996/011174 | 4/1996 |
| WO | 2005/031066 | 4/2005 |
| WO | 2008/124375 | 10/2008 |

OTHER PUBLICATIONS

Hattori H., et al., "Solid base catalysts: generation of basic sites and application to organic synthesis", Applied Catalysis, A: General 222, pp. 247-259, 2001.

Beres A., et al., "Layered double hydroxides and their pillared derivatives—materials for solid base catalysis; synthesis and characterization", Applied Catalysis, A: General 182, pp. 237-247, 1999.

U.S. Appl. No. 16/767,829, filed May 28, 2020.

* cited by examiner

PROCESSES FOR ISOMERIZING ALPHA OLEFINS

CROSS REFERENCE TO RELATED APPLICATIONS

This application claims the benefit of priority from U.S. Provisional Application No. 62/598,596, filed Dec. 14, 2017, which is incorporated herein by reference.

FIELD

The present disclosure relates to processes for isomerizing alpha olefins to produce an isomerization mixture comprising internal olefins.

BACKGROUND

Internal olefins are commercially valuable for use in a variety of applications, such as paper sizing agents and drilling fluids. For example, internal olefin based drilling fluids exhibit a number of enhanced properties, such as lower pour point, compared to alpha olefin based drilling fluids. For instance, U.S. Pat. No. 5,589,442 discloses synthetic hydrocarbon-based drilling fluids comprising mostly linear $C_{14}$ to $C_{18}$ olefins.

Internal olefins may be produced via the isomerization of alpha olefins. In the isomerization of alpha olefins to internal olefins for use in drilling fluids, it is desirable to produce an isomerization mixture having a combination of a reduced pour point while maintaining acceptable biodegradability. The pour point of the isomerization mixture generally decreases with increasing conversion of alpha olefins to internal olefins and with increasing formation of branched olefins. In contrast, the biodegradability of the isomerization mixture generally increases with decreased formation of branched olefins, particularly those having extended branching.

Accordingly, there is a need for highly active and selective methods of isomerizing alpha olefins to internal olefins at high conversion and with a controlled amount of branched olefin formation. References of potential interest may include: U.S. Pat. Nos. 5,741,759; 5,965,783; 6,054,629; 7,956,229; 5,107,047; 5,246,566; 4,749,819; 5,177,281; and U.S. Pat. Pub. No. U.S. 2005/0070747.

SUMMARY

According to the present disclosure, it has now been found that employing molecular sieve catalysts having dual acid functionalities in the isomerization of $C_{14}$-$C_{24}$ alpha olefins advantageously allows for the isomerization to be conducted under mild process conditions, particularly at low temperature, and furthermore that such catalysts are particularly effective in controlling branched olefin formation in the produced isomerization mixture.

Thus, in one aspect, the present disclosure relates to a process for isomerizing one or more $C_{14}$-$C_{24}$ alpha olefins to produce an isomerization mixture comprising one or more $C_{14}$-$C_{24}$ internal olefins, the process comprising contacting an olefinic feed comprising the one or more $C_{14}$-$C_{24}$ alpha olefins with a catalyst under isomerization conditions, wherein the catalyst comprises a molecular sieve having an MWW framework.

In a further aspect, the present disclosure relates to a drilling fluid composition comprising the isomerization mixture produced by the foregoing process.

In a further aspect, the present disclosure relates to a paper sizing composition comprising the isomerization mixture produced by the foregoing process.

In yet a further aspect, the present disclosure relates to an olefinic mixture comprising about 60 wt % or more of linear internal olefins based on the weight of the mixture, from about 0 wt % to about 30 wt % of branched olefins based on the weight of the mixture, and less than about 10 wt % of linear alpha olefins based on the weight of the mixture.

In yet another further aspect, the present disclosure relates to an olefinic mixture comprising about 41 wt % or more of linear internal olefins based on the weight of the mixture, from about 0 wt % to about 30 wt % of branched olefins based on the weight of the mixture, and from about 10 wt % to about 29 wt % of linear alpha olefins based on the weight of the mixture.

DETAILED DESCRIPTION OF THE PREFERRED EMBODIMENTS

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Definitions

For the purpose of this specification and appended claims, the following terms are defined.

The term "hydrocarbon" means a class of compounds containing hydrogen bound to carbon, and encompasses (i) saturated hydrocarbon compounds; (ii) unsaturated hydrocarbon compounds; and (iii) mixtures of hydrocarbon compounds (saturated and/or unsaturated), including mixtures of hydrocarbon compounds having different values of n, i.e. differing carbon numbers.

As used herein, a "carbon number" refers to the number of carbon atoms in a hydrocarbon. Likewise, a "$C_x$" hydrocarbon is one having x carbon atoms (i.e., carbon number of x), and a "$C_x$-$C_y$" or "$C_{x-y}$" hydrocarbon is one having from x to y carbon atoms.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "olefin," alternatively referred to as "alkene," refers to a branched or unbranched unsaturated hydrocarbon having one or more carbon-carbon double bonds. A simple olefin comprises the general formula $C_nH_{2n}$, where n is 2 or greater. Examples of olefins include, but are not limited to ethylene, propylene, butylene, pentene, hexene and heptene. "Olefin" is intended to embrace all structural isomeric forms of an olefin. For example, butylene encompasses but-1-ene, (Z)-but-2-ene, etc.

As used herein, the term "molecular sieve" is used synonymously with the term "zeolite" or "microporous crystalline material."

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, kinematic viscosity (KV) is measured using ASTM standard D-445 and reported at temperatures of 100° C. (KV100), 40° C. (KV40) and/or 0° C. (KV0).

As used herein, pour point is measured according to ASTM D5950.

Various embodiments described herein provide processes for the production of one or more $C_{14}$-$C_{24}$ internal olefins via isomerization, typically catalytic isomerization, of one or more $C_{14}$-$C_{24}$ alpha olefins. It has been found that employing molecular sieve catalysts having an MWW framework in the isomerization advantageously allows for the isomerization to be conducted under mild process conditions, particularly at low temperature. Conducting the isomerization at a low temperature provides several benefits, such as reducing energy usage of the process and improving selectivity to desired products in the resulting isomerization mixture. Additionally, it has been found that such catalysts are particularly effective in controlling branched olefin formation in the produced isomerization mixture. Without wishing to be bound by theory, it is believed that the aforementioned advantages result from the dual acid functionalities, i.e., both in channels and surface pockets, characteristic of catalysts having an MWW framework. Generally, the resulting isomerization mixture comprises a minimized branched olefin content in a range low enough to maintain biodegradability properties of the mixture while high enough to maintain an acceptably low pour point. For example, the isomerization mixture advantageously comprises branched olefins in a range from about 0 wt % to about 30 wt %, such as from about 10 wt % to about 30 wt % based on the weight of the isomerization mixture.

Supply of Alpha Olefins

Generally, the alpha olefins supplied to the isomerization have a carbon number ranging from 14 to 24, more preferably from 14 to 20, more preferably from 15 to 18, and ideally from 16 to 18. Preferably, the alpha olefins supplied to the isomerization are linear alpha olefins.

Typically, the one or more $C_{14}$-$C_{24}$ alpha olefins are provided in an olefinic feed. Suitable olefinic feeds for use in various embodiments of the present invention comprise (or consist essentially of, or consist of) $C_{14}$-$C_{24}$ alpha olefins, preferably $C_{14}$-$C_{20}$ alpha olefins, such as $C_{15}$-$C_{18}$ alpha olefins, ideally $C_{16}$-$C_{18}$ alpha olefins. In any embodiment, at least about 50 wt %, preferably at least about 60 wt %, more preferably at least about 80 wt %, more preferably at least about 85 wt %, more preferably at least about 95 wt %, more preferably at least about 99 wt % of the olefinic feed is composed of alpha olefins, preferably alpha olefins, having any of the aforementioned $C_x$-$C_y$ ranges (i.e., any of the aforementioned numbers of carbon atoms) based on the total weight of the olefinic feed. For example, in any embodiment the olefinic feed may comprise from about 50 wt % to about 100 wt %, such as from about 75 wt % to about 90 wt %, of alpha olefins, preferably linear alpha olefins, having any of the aforementioned $C_x$-$C_y$ ranges based on the total weight of the olefinic feed. Particularly preferable olefinic feeds may comprise $C_{16}$-$C_{18}$ alpha olefins, ideally $C_{16}$/$C_{18}$ linear alpha olefin mixtures. In such aspects, the olefinic feed typically comprises at least about 40 wt % of $C_{16}$ alpha olefins, more preferably at least about 60 wt %, such as at least about 65 wt % of $C_{16}$ alpha olefins (preferably linear $C_{16}$ alpha olefins) based on the total weight of the olefinic feed and, additionally or alternatively, at most about 60 wt %, more preferably at most about 40 wt %, such as at most about 35 wt % of $C_{18}$ alpha olefins (preferably linear $C_{18}$ alpha olefins) based on the total weight of the olefinic feed, such as from about 60 wt % or from about 65 wt % to 75 wt % $C_{16}$ alpha olefins and from about 25% to about 40 wt % or to about 35 wt % $C_{18}$ alpha olefins based on the total weight of the olefinic feed.

In any embodiment, the olefinic feed preferably has an average carbon number (by weight, as measured by GC-MS) of greater than or equal to 14, preferably greater than or equal to 16, such as from 14 to 24.

Typically, the olefinic feed is substantially linear. For example, the olefinic feed typically has a branched olefin content of less than 10 wt % based on the total weight of the olefinic feed, preferably less than about 8 wt %, more preferably less about 4 wt %, such as from 0 wt % to 10 wt % branched olefin content based on the total weight of the olefinic feed.

Preferably, the olefinic feed is pretreated prior to isomerization to remove moisture, oxygenates, nitrates, and other impurities that could deactivate the isomerization catalyst. Typically, the pretreatment is performed by passing the feed can be through a guard bed that contains a molecular sieve. Typically, the pretreated feed comprises less than about 50 ppmw water based on the weight of the feed, more preferably less than about 25 ppmw.

Isomerization Catalyst

Generally, the isomerization is conducted in the presence of a catalyst. Typically, the isomerization catalyst comprises (or consists essentially of, or consists of) a molecular sieve of the MWW family Preferably, the molecular sieve is of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. Nos. 4,954,325, 7,883,686, and 8,021,643), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof. In an especially preferred embodiment, the isomerization catalyst comprises (or consists essentially of, or consists of) a molecular sieve selected from the group consisting of MCM-22, MCM-49 and MCM-56, such as MCM-22 or MCM-49, in particular MCM-22.

Preferably, the molecular sieve is highly acidic. For example, preferably the molecular sieve has a $SiO_2/Al_2O_3$ molar ratio of less than about 50, or less than about 40, or less than about 25, or less than about 10, such as from about 10 to about 50, or from about 20 to about 40.

The isomerization catalyst may be composited with a porous matrix binder material such as clay and/or inorganic oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable inorganic oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition. Typically, the binder material may be present from about 0 wt % to about 90 wt % based on the weight of the isomerization catalyst, such as from about 20 wt % to about 50 wt %.

Typically, the isomerization catalyst is free or substantially free of additional components apart from the molecular, binder (if present), and optionally, trace amounts of alkali and/or alkali earth metals or compounds thereof. For example, in any embodiment the isomerization catalyst may be free or substantially free from promoters, such as noble metals and transition metals in metal or metal oxide form, e.g., platinum, palladium, ruthenium, iron, cobalt, and nickel. For instance, preferably the isomerization catalyst may comprise a combined platinum, palladium, ruthenium, iron, cobalt, and nickel content of less than about 0.5 wt % based on the weight of the isomerization catalyst, more preferably less than about 0.1 wt % or less than about 0.01 wt %.

Isomerization of Alpha Olefins

The isomerization reaction can be conducted in a wide range of reactor configurations including fixed bed (single or in series) and fluidized bed, preferably fixed bed. In addition, the isomerization can be conducted in a single reaction zone or in a plurality of reaction zones.

Typically, the isomerization is conducted under conditions suitable to maintain the reaction medium in the liquid phase. Preferably, the isomerization is conducted under mild process conditions, particularly at low temperature. Suitable reaction temperatures range from about 50° C. to about 200° C., such as from about 100° C. to about 180° C., or from about 110° C. to about 170° C., or from about 130° C. to about 150° C., while suitable isomerization pressures range from about 2 kPa absolute to about 7,000 kPa absolute, such as from about 5 psig (136 kPa-a) to about 200 psig (1480 kPa-a). Preferably, the olefinic feed is supplied to the reaction at a weight hourly space velocity (WHSV) ranging from about 1 $h^{-1}$ to about 50 $h^{-1}$, more preferably from about 2 $h^{-1}$ to about 20 $h^{-1}$.

Typically, the isomerization exhibits a high single-pass rate of conversion (measured as 100 minus the remaining amount of LAO expressed in wt %, as measured by GC). For example, preferably the single-pass rate of conversion of the one or more $C_{14}$-$C_{24}$ alpha olefins is at least about 40%, more preferably at least about 50%, and ideally at least about 71% or 75%, such as at least about 90%. In such aspects, the isomerization can be conveniently conducted in the absence of recycle, i.e., without recycling any portion of the produced isomerization mixture. Preferably, conducting the isomerization without recycle provides several process advantages, such as increasing process reliability and reducing operating costs.

In a first alternative, the isomerization conversion level can be maximized, for instance to a conversion level of more than about 90%, in particular of at least about 91% or at least about 92% or at least about 93% or at least about 94% or even at least about 95%. This first alternative results in an isomerization mixture containing less than about 10 wt %, such as less than 5 wt %, or even less than 3 wt % of linear alpha olefins based on the weight of the mixture. This first alternative is especially advantageous as it results in isomerization mixtures having especially low pour points of less than −10° C., such as of −12° C., or even −16° C., −18° C., −20° C. or −22° C. This is of special interest for applications that are conducted under cold conditions or climate.

In a second alternative, the isomerization conversion level can be limited to a maximal amount, for instance with a conversion level of maximum 90%, such as a conversion level of from about 50% to about 90%, for instance from about 71% to about 90%, especially from about 80% to about 90%, such as from about 85% to about 90%. This second alternative typically results in an isomerization mixture containing at least about 10 wt %, such as from about 10 wt % to about 20 wt %, and ideally from about 10 wt % to about 15 wt %, of linear alpha olefins based on the weight of the mixture. This second alternative is especially advantageous for the production of isomerization mixtures having a lower viscosity as compared to the isomerization mixtures obtained by the first alternative, using the same feed and reaction conditions. For instance, starting from an olefinic feed comprising a $C_{16}/C_{18}$ linear alpha olefins mixture, this second alternative allows for the production of isomerization mixtures having a kinematic viscosity at 40° C. (KV40) of less than 3.4 cSt, in particular from about 3.0 cSt to less than 3.4 cSt, such as from about 3.0 or 3.05 or 3.1 cSt to less than 3.4 cSt. Such isomerization mixtures are especially suitable as drilling fluids, in particular as anaerobic biodegradable drilling fluid products.

Preferably, the isomerization reaction is highly selective to the desired internal olefin products, particularly linear internal olefins, and exhibits minimal side reactions, such as skeletal isomerization, oligomerization, and cracking. For example, typically less than about 10 wt % of $C_{14}$-$C_{24}$ alpha olefins present in the olefinic feed are converted to product having a lower or higher carbon number. Additionally or alternatively, typically from about 5 wt % to about 30 wt % of linear $C_{14}$-$C_{24}$ alpha olefins present (if any) in the olefinic feed are converted to branched olefins.

Isomerization Mixture

The resulting isomerization mixture obtained via isomerization of the one or more $C_{14}$-$C_{24}$ alpha olefins according to any one or more of the foregoing embodiments typically comprises (or consists essentially of, or consists of) linear internal olefins, and optionally, branched olefins, e.g., branched internal olefins. For example, the isomerization mixture typically comprises at least about 40 wt %, preferably at least about 60 wt %, more preferably at least about 80 wt %, such as at least about 85 wt %, or at least about 95 wt %, or even at least about 99 wt % of linear internal olefins based on the total weight of the isomerization mixture. The isomerization mixture preferably has a branched olefin content of less than about 35 wt %, preferably less than about 20 wt %, such as less than about 10 wt %, or less than about 8 wt % based on the total weight of the isomerization mixture, such as from about 5 wt % to about 30 wt %, or from about 8 wt % to about 15 wt %, or from about 0 wt % to about 10 wt %.

The isomerization product may also contain some amount of residual $C_{14}$-$C_{24}$ alpha olefins. Preferably, the isomerization mixture comprises a residual alpha olefin content of less than about 35 wt %. In a first alternative, the isomerization mixture contains less than about 10 wt %, and ideally less than about 5 wt %, such as less than about 3 wt % of residual linear alpha olefins based on the total weight of the isomerization mixture. In a second alternative, the isomerization mixture contains from about 10 wt % to about 29 wt %, preferably from about 10 wt % to about 20 wt %, and ideally from about 10 wt % to about 15 wt %, of residual linear alpha olefins based on the total weight of the isomerization mixture.

In the present processes, it is found that molecular sieves having an MWW framework are particularly active for the isomerization of $C_{14}$-$C_{24}$ linear alpha olefins. In addition, such catalysts exhibit improved selectivity towards linear internal olefins while also providing improved control of branched olefin formation.

For example, in the first alternative, using a molecular sieve having an MWW framework in the isomerization of $C_{16}$ and/or $C_{18}$ LAO feed having a branched olefin content from about 6 wt % to about 8 wt %, such as 65 wt % $C_{16}$/35 wt % $C_{18}$ LAO feed having a branched olefin content from about 6 wt % to about 8 wt %, or of 60 wt % $C_{16}$/40 wt % $C_{18}$ LAO feed having a branched olefin content from about 6 wt % to about 8 wt %, it is found that the resulting isomerization mixture may comprise:
  at least 60 wt %, such as at least 70 wt %, for example at least 75 wt % or at least 80 wt % of linear internal olefins;
  from 10 wt % to 30 wt % of branched olefins, such as from 10 wt % to 25 wt %, or from about 15 wt % to about 25 wt %, or from about 15 wt % to about 20 wt %, or from about 10 wt % to about 20 wt %, or from about 10 wt % to about 15 wt %; and
  less than 10 wt %, such as less than 5 wt %, for example less than 3 wt % of linear alpha olefins.

Accordingly, in a first alternative, olefinic mixtures produced in accordance with the processes of the present disclosure may advantageously comprise at least about 60 wt %, such as at least about 70 wt % or at least about 75 wt % or at least about 80 wt % of $C_{14}$-$C_{24}$ linear internal olefins, preferably $C_{16}$-$C_{18}$ linear internal olefins; from about 10 wt % to about 30 wt % of branched olefins, such as from about 10 wt % to about 25 wt %, or from about 15 wt % to about 25 wt %, or from about 15 wt % to about 20 wt %; and less than 10 wt %, such as less than 5 wt %, for example less than 3 wt % of linear alpha olefins, when prepared from a LAO feed having a branched olefin content from about 6 wt % to about 8 wt %. Should the LAO feed have a branched olefin content lower than 6-8 wt %, the resulting isomerization mixture would have a lower branched olefin content. For instance, if the isomerization of a LAO feed having a branched olefin content of 7 wt % results in an isomerization mixture having a branched olefin content of 10 wt %, starting from a similar LAO feed having a branched olefin content of 2 wt % would result in an isomerization mixture having a branched olefin content of 5 wt %. Therefore, olefinic mixtures produced in accordance with the first alternative of the processes of the present disclosure may also advantageously comprise at least about 60 wt %, such as at least about 70 wt % or at least about 75 wt % or at least about 80 wt % of $C_{14}$-$C_{24}$ linear internal olefins, preferably $C_{16}$-$C_{18}$ linear internal olefins; less than 10 wt %, such as less than 5 wt %, for example less than 3 wt % of linear alpha olefins; and from about 0 wt % to about 35 wt % or from about 0 wt % to about 30 wt % or from about 0 wt % to about 25 wt % or to about 10 wt % of branched olefins.

In the second alternative, using a molecular sieve having an MWW framework in the isomerization of $C_{16}$ and/or $C_{18}$ LAO feed having a branched olefin content from about 6 wt % to about 8 wt %, such as 65 wt % $C_{16}$/35 wt % $C_{18}$ LAO feed having a branched olefin content from about 6 wt % to about 8 wt %, or of 60 wt % $C_{16}$/40 wt % $C_{18}$ LAO feed having a branched olefin content from about 6 wt % to about 8 wt %, it is found that the resulting isomerization mixture may comprise:

at least 41 wt %, such as at least 55 wt %, for example at least 60 wt % or at least 65 wt % of linear internal olefins;
from 10 wt % to 30 wt % of branched olefins, such as from 15 wt % to 30 wt %, or from about 10 wt % to about 25 wt %; and
from about 10 wt % to about 29 wt %, such as from about 10 wt % to about 20 wt %, for instance from about 10 wt % to about 15 wt %, of linear alpha olefins.

Accordingly, in a second alternative, olefinic mixtures produced in accordance with the processes of the present disclosure may advantageously comprise at least about 41 wt %, such as at least about 55 wt % or at least about 60 wt % or at least about 65 wt % of $C_{14}$-$C_{24}$ linear internal olefins, preferably $C_{16}$-$C_{18}$ linear internal olefins; from about 10 wt % to about 30 wt % of branched olefins, such as from 15 wt % to about 30 wt %, or from about 10 wt % to about 25 wt %; and from about 10 wt % to about 29 wt %, such as from about 10 wt % to about 20 wt %, for example from about 10 wt % to about 15 wt % of linear alpha olefins, when prepared from a feed having a branched olefin content from about 6 wt % to about 8 wt %. Should the LAO feed have a branched olefin content lower than 6-8 wt %, the resulting isomerization mixture would have a proportionally lower resulting branched olefin content. Should the LAO feed have a branched olefin content lower than 6-8 wt %, the resulting isomerization mixture would have a lower branched olefin content. For instance, if the isomerization of a LAO feed having a branched olefin content of 7 wt % results in an isomerization mixture having a branched olefin content of 10 wt %, starting from a similar LAO feed having a branched olefin content of 2 wt % would result in an isomerization mixture having a branched olefin content of 5 wt %. Therefore, olefinic mixtures produced in accordance with the second alternative of the processes of the present disclosure may also advantageously comprise at least about 41 wt %, such as at least about 55 wt % or at least about 60 wt % or at least about 65 wt % of $C_{14}$-$C_{24}$ linear internal olefins, preferably $C_{16}$-$C_{18}$ linear internal olefins; from about 10 wt % to about 29 wt %, such as from about 10 wt % to about 20 wt %, for example from about 10 wt % to about 15 wt % of linear alpha olefins; and from about 0 wt % to about 35 wt % or from about 0 wt % to about 30 wt % or from about 0 wt % to about 25 wt % or to about 10 wt % of branched olefins.

In any embodiment, the obtained isomerization mixture may be particularly useful in drilling fluid compositions and paper sizing compositions. Preferred isomerization mixtures suitable for drilling fluid compositions generally comprise 50 wt % or more of $C_{16}$-$C_{18}$ linear internal olefins. Such mixtures may be particularly useful as the oil-phase in drilling fluid compositions comprising oil-based drilling emulsions. In an especially preferred embodiment, the isomerization mixture comprises, in the first alternative, about 60 wt % or more, in particular about 70 wt % or more, or about 75 wt % or more, or about 80 wt % or more of $C_{16}$-$C_{18}$ linear internal olefins; from about 0 wt % or from about 10 wt % to about 30 wt %, of $C_{16}$-$C_{18}$ branched olefins; and less than about 10 wt %, such as less than about 5 wt % of $C_{16}$-$C_{18}$ linear alpha olefins; or, in the second alternative, about 41 wt % or more, in particular about 55 wt % or more, or about 60 wt % or more, or about 65 wt % or more of $C_{16}$-$C_{18}$ linear internal olefins; from about 0 wt % or from about 10 wt % to about 30 wt %, of $C_{16}$-$C_{18}$ branched olefins; and from about 10 wt % to about 29 wt %, such as from about 10 wt % to about 20 wt % or from about 10 to about 15 wt % of $C_{16}$-$C_{18}$ linear alpha olefins. These isomerization mixtures are especially suitable for drilling fluid compositions.

When used for drilling fluid compositions, the isomerization mixture may generally exhibit any one or more of the following properties:

KV100 within the range from about 1 cSt to about 2 cSt, preferably from about 1 to about 1.1 cSt to about 1.5 cSt.

KV40 within the range from about 2 cSt to about 5 cSt, in particular from about 3 cSt to about 5 cSt, more particularly from about 3.0 cSt to 4.0 cSt, such as, in a first alternative, from about 3.4 cSt to about 5.0 cSt or to about 4.0 cSt or, in a second alternative, from about 3.0 or 3.05 or 3.1 cSt to less than 3.4 cSt, more particularly from 3.0 to 3.35 cSt such as from 3.1 to 3.3 cSt.

Pour point of −6° C. or less, such as −10° C. or less, such as −12° C. or less, such as −15° C. or less.

Additionally or alternatively, when used for drilling fluid compositions the isomerization mixture is typically biodegradable under aerobic and preferably anaerobic conditions. Particularly preferably, the isomerization mixture and drilling fluid compositions comprising the same meet or exceed the anaerobic biodegradability standard set forth in the Marine Closed Bottle Biodegradation Test System: EPA METHOD 1647.

The following examples illustrate the present invention. Numerous modifications and variations are possible and it is to be understood that within the scope of the appended claims, the invention may be practiced otherwise than as specifically described herein.

EXAMPLES

Gas Chromatography Procedure

Liquid samples from the reactor effluent were analyzed on an Agilent 7890 Gas Chromatograph (GC) equipped with FID detectors and automatic liquid samplers (ALS). Two GC methods were employed to analyze the samples—one for measuring the linear alpha olefin (LAO) content and the other for measuring the branched olefin (BO) content. The typical injection size for both methods was about 0.2 μl.

For the LAO content measurement method, the column used was Agilent DB-WAX (60 m×250 μm×0.25 μm). The GC was operated in constant flow mode at 40 psi (280 kPa) inlet pressure and with column flow of 1.839 mL/min using helium as a carrier gas. The following oven procedure was used:

Initial temperature of 140° C., hold for 17 minutes;
Ramp at 25° C./min to 240° C., hold for 8 minutes;
Total analysis time of 29 minutes.

For the BO content measurement method, liquid sample was first fully hydrogenated to saturated material, from which the BO content was determined by analyzing the total branched aliphatic material. The column used was Agilent HP-1 (60 m×250 μm×1 μm) and the inlet liner was a split inlet liner (obtained from Agilent) that was pre-packed with 1 cm height 1% Pt/$Al_2O_3$. The GC was operated in ramped pressure mode with an initial pressure of 20 psi (140 kPa) to 50 psi (340 kPa) at 7 psi/min (50 kPa/min) using hydrogen as a carrier gas. The following oven procedure was used:
Initial temperature of 140° C., hold for 17 minutes;
Ramp at 25° C./min to 240° C., hold for 8 minutes;
Total analysis time of 29 minutes.

In the event that oligomerized molecules, such as and mostly dimers, would be present in the product stream, the BO content measured from the above method is further adjusted by the following: $BO_{adj.}=(100-Dimer)*BO$. Overall BO content when dimer is present is calculated as the sum of the adjusted BO and Dimer make. For Dimer content measurement, the column used was Restek Rxi-1HT (30 m×250 μm×0.10 μm, 13951). The GC was operated in constant flow mode at 9.2 psi inlet pressure and with column flow of 1.6 mL/min using hydrogen as carrier gas. The following oven procedure was used:
Initial temperature of 40° C., hold for 5 minutes;
Ramp at 20° C./min to 360° C., hold for 20 minutes;
Total analysis time of 41 minutes.

The LIO content can be assessed as LIO=100−LAO content−BO content.

Measurement of Alpha Value

The Alpha Value tests for the materials or compositions in the Examples were performed in accordance with the methods described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test included a constant temperature of 538° C. and a variable flow rate as described in detail in the Journal of Catalysis, Vol. 61, p. 395 (1980).

Measurement of Total Surface Area by BET

The total BET was measured by nitrogen adsorption/desorption with a Micromeritics Tristar II 3020 instrument after degassing of the calcined catalyst material for 4 hrs at 350° C. More information regarding the method can be found, for example, in "Characterization of Porous Solids and Powders: Surface Area, Pore Size and Density", S. Lowell et al., Springer, 2004.

Example 1: Synthesis of MCM-22 Crystals at Medium Crystallization Temperature

A hydrothermal mixture was prepared from water, hexamethylethyleneimine (HMI) (Sigma-Aldrich, 99%), Ultrasil™ silica, 45% sodium aluminate solution, and 50% sodium hydroxide solution according to example 1 of U.S. Pat. No. 8,021,643. The mixture had the following molar composition:

| | |
|---|---|
| $SiO_2/Al_2O_3$ | ~30 |
| $H_2O/SiO_2$ | ~19.8 |
| $OH^-/SiO_2$ | ~0.17 |
| $Na^+/SiO_2$ | ~0.17 |
| $HMI/SiO_2$ | ~0.35 |

The mixture was crystallized at 150° C. in an autoclave with stirring at 250 rotations per minute (rpm) for 72 hours. After crystallization, the hydrothermal reaction mixture slurry was filtered, washed with deionized (DI) water and dried at 120° C. The XRD pattern of the as-synthesized material showed the typical pure phase of MCM-22 topology. The SEM of the as-synthesized material showed typical morphology of layered crystals. The resulting as-synthesized MCM-22 crystals had a $SiO_2/Al_2O_3$ molar ratio of about 23.

Example 2: Synthesis of MCM-22 Crystals at High Crystallization Temperature

A hydrothermal reaction mixture was prepared from water, hexamethylethyleneimine (HMI) (Sigma-Aldrich, 99%), Ultrasil™ silica, 45% sodium aluminate solution, and 50% sodium hydroxide solution according to example 2 of U.S. Pat. No. 8,021,643.

The mixture had the following molar composition:

| | |
|---|---|
| $SiO_2/Al_2O_3$ | ~30 |
| $H_2O/SiO_2$ | ~13 |
| $OH^-/SiO_2$ | ~0.15 |
| $Na^+/SiO_2$ | ~0.15 |
| $HMI/SiO_2$ | ~0.20 |

The mixture was crystallized at 170° C. in an autoclave with stirring at 250 rotations per minute (rpm) for 24 hours. After crystallization, the hydrothermal reaction mixture slurry was filtered, washed with deionized (DI) water and dried at 120° C. The XRD pattern of the as-synthesized material showed the typical pure phase of MCM-22 topology. The SEM of the as-synthesized material showed typical morphology of layered crystals. The resulting as-synthesized MCM-22 crystals had a $SiO_2/Al_2O_3$ molar ratio of about 24.1.

Example 3: Synthesis of MCM-49 Crystals at High Crystallization Temperature

A hydrothermal reaction mixture was prepared from water, hexamethylethyleneimine (HMI) (Sigma-Aldrich Company, 99%), Ultrasil™ silica, 45% sodium aluminate solution, and 50% sodium hydroxide solution according to U.S. Pat. No. 5,236,575.

The mixture had the following molar composition:

| | |
|---|---|
| $SiO_2/Al_2O_3$ | ~21 |
| $H_2O/SiO_2$ | ~14.5 |
| $OH^-/SiO_2$ | ~0.18 |
| $Na^+/SiO_2$ | ~0.18 |
| $HMI/SiO_2$ | ~0.19 |

The mixture was crystallized at 320° F. (160° C.) in an autoclave with stirring at 250 rotations per minute (rpm) for 72 hours. After crystallization, the hydrothermal reaction mixture slurry was filtered, washed with deionized (DI) water and dried at 250° F. (121° C.). The XRD pattern of the as-synthesized material showed the typical pure phase of MCM-49 topology. The SEM of the as-synthesized material showed typical morphology of layered crystals. The resulting as-synthesized MCM-22 crystals had a $SiO_2/Al_2O_3$ molar ratio of about 19.1.

Example 4: Preparation of MCM-22 Alumina-Bound Catalyst Using High Surface Area Alumina Binder (Catalyst A)

65 parts by weight, on a calcined at 538° C. basis, of the as-synthesized MCM-22 crystals prepared in Example 1 were mulled with 35 parts by weight, on a calcined at 538° C. basis, of Versal-300 pseudoboehmite alumina binder (commercially available from UOP LLC). A sufficient amount of water was added to make an extrudable paste, after which the resulting paste was extruded into ¹⁄₁₆" (0.16 cm) cylinder extrudates and then dried at 121° C. overnight.

The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 520 and surface area of ~445 m$^2$/g.

Example 5: Preparation of MCM-22 Alumina-Bound Catalyst Using Low Surface Area Alumina Binder (Catalyst B)

65 parts by weight, on a calcined at 538° C. basis, of the as-synthesized MCM-22 crystals prepared in Example 1 were mulled with 35 parts by weight, on a calcined at 538° C. basis, of Catapal™-200 boehmite alumina binder (commercially available from Sasol Performance Chemicals). A sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 620 and surface area of 432 m$^2$/g.

Example 6: Preparation of MCM-22 Silica-Bound Catalyst Using Low Acidity Silica Binder (Catalyst C)

65 parts by weight, on a calcined at 538° C. basis, of the as-synthesized MCM-22 crystals prepared in Example 1 were mulled with 35 parts by weight, on a calcined at 538° C. basis, of Ultrasil™ silica binder. A sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 280 and surface area of ~302 m$^2$/g.

Example 7: Preparation of MCM-49 Alumina-Bound Catalyst Using High Surface Area Alumina Binder (Catalyst D)

80 parts by weight, on a calcined at 538° C. basis, of the as-synthesized MCM-49 crystals prepared in Example 3 were mulled with 20 parts by weight, on a calcined at 538° C. basis, of Versal-300 pseudoboehmite alumina binder (commercially available from UOP LLC). A sufficient amount of water was added to make an extrudable paste, after which the resulting paste was extruded into 1/20" (0.13 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 520 and surface area of ~536 m$^2$/g.

Example 8: Preparation of MCM-22 Alumina-Bound Catalyst Using High Surface Area Alumina Binder and New Extrusion Insert (Catalyst E)

80 parts by weight, on a calcined at 538° C. basis, of the as-synthesized MCM-22 crystals prepared in Example 1 were mulled with 20 parts by weight, on a calcined at 538° C. basis, of Versal-300 pseudoboehmite alumina binder (commercially available from UOP LLC). A sufficient amount of water was added to make an extrudable paste, after which the resulting paste was extruded into 1/20" (0.13 cm) expanded trilobe (i.e., with higher specific surface area) extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 790 and surface area of ~512 m$^2$/g.

Examples 9-11: Isomerization of $C_{16}/C_{18}$ (65:35) LAO Feed in a Fixed Bed Reactor The isomerization tests described in Examples 9-11 were carried out in a continuous, isothermal, tubular fixed bed reactor. In each experiment, the formulated catalyst prepared in Example 4 (Catalyst A) was loaded into the reactor in the amount specified in Table 1, along with approximately 15-20 g of silicon carbide (SiC). The catalyst was loaded between two separate sections of SiC such that it was securely positioned in the isothermal zone of the reactor. A 65 wt % $C_{16}$/35 wt % $C_{18}$ LAO feed (a blend of Alphaplus™ 1-Hexadecene and Alphaplus™ 1-Octadecene, both available from ChevronPhillips Chemical Company LLC) containing ~7 wt % BO (as determined by GC) was then introduced into the reactor at a WHSV of 2.5 h$^{-1}$. The isomerization reaction was conducted at a temperature of either 130° C. or 150° C. and a pressure of 20 psig (239 kPa-a).

Figure 1:
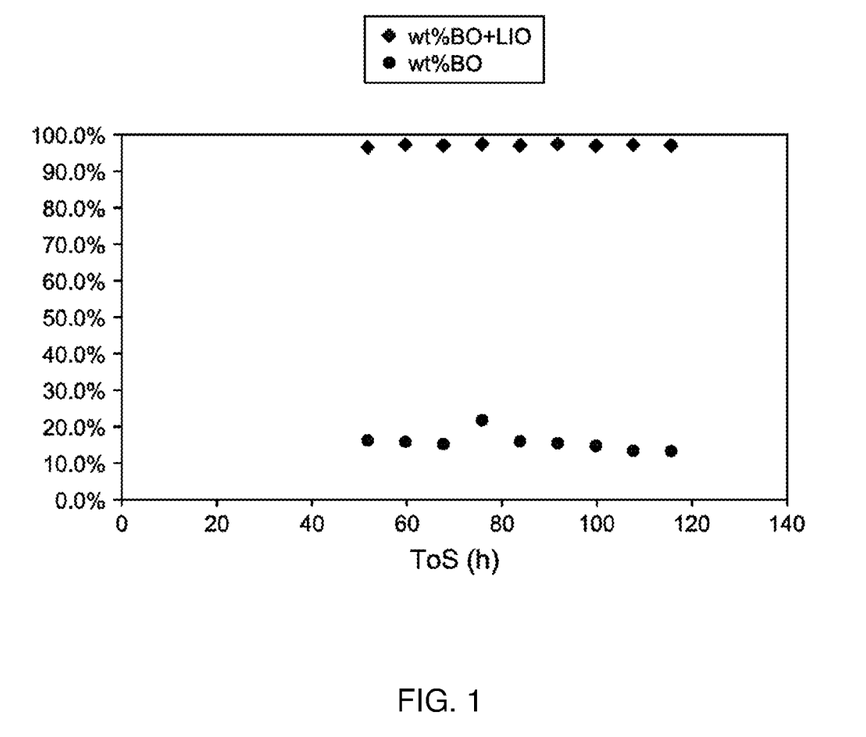
FIG. 1 depicts the linear internal olefin and branched olefin concentrations of the isomerization mixture against time on stream (TOS) produced in the isomerization reaction conducted in Example 9.
Figure 2:
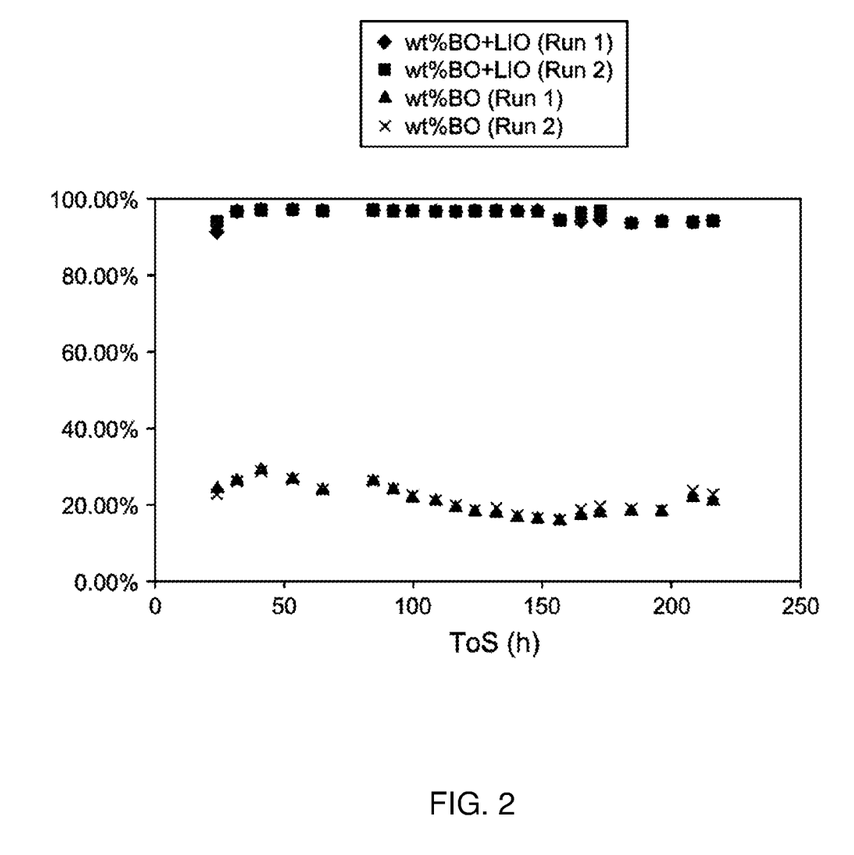
FIG. 2 depicts the linear internal olefin and branched olefin concentrations of the isomerization mixture against time on stream (TOS) produced in the isomerization reactions conducted in Example 10.

Table 1 summarizes the catalyst loading and reaction conditions for Examples 9-11. The relative amounts of unreacted LAO, linear internal olefins (LIO), and branched olefins (BO) in the produced isomerization mixture against time on stream for Examples 9 and 10 are depicted in FIG. 1 and FIG. 2. Table 2 summarizes a comparison of the composition and pour point of the resulting isomerization mixtures at 70 hr TOS for Example 11 with that of a commercially available isomerized $C_{16}/C_{18}$ alpha olefin reference fluid, AlphaPlus™ $C_{16}$-$C_{18}$ ISA 65:35, available from ChevronPhillips Chemical Company.

TABLE 1

|  | Ex. 9 | Ex. 10 (Runs 1 and 2) | Ex. 11 |
|---|---|---|---|
| Catalyst Loading (g) | 1.54 | 3.08 | 1.54 |
| T (° C.) | 130 | 150 | 130 |
| Reaction Duration (h) | 116 | 220 | 70 |

TABLE 2

|  | Ex. 11 | $C_{16}/C_{18}$ Reference Fluid |
|---|---|---|
| LIO (wt %) | ~83.7 | 65.0 |
| BO (wt %) | ~13.7 | 31.0 |
| LAO (wt %) | ~2.6 | 4.0 |
| Point Point (° C.) | −19.5 | −12.0 |

As can be seen from FIG. 1 and FIG. 2 and Table 2, very high conversion of linear alpha olefins was observed in each of Examples 9-11. Particularly, the LIO and BO content in the isomerization mixture produced in each of these examples maintained a combined total in excess of 94 wt % throughout the entirety of the sampling periods. Additionally, controlled BO content levels were maintained throughout the entirety of the sampling periods, e.g., from 14 to 21 wt % in Example 9, from 15 to 30 wt % in Example 10, and 13.7 wt % in Example 11. Such controlled formation of BO resulted in a desirable decrease in pour point, as illustrated by the −19.5° C. pour point observed in the isomerization mixture of Example 11 (having a BO content of ~13.7 wt %), representing a 7.5° C. decrease in pour point versus that of the $C_{16}/C_{18}$ reference fluid (having a BO content of 31.0 wt %).

Example 12: Isomerization of $C_{16}/C_{18}$ (60:40) LAO Feed in a Fixed Bed Reactor The isomerization test described in Example 12 was carried out similarly to that of examples 9-11. The formulated catalyst prepared in Example 4 (Catalyst A, 1.0 g) was loaded into the reactor, along with approximately 15-20 g of silicon carbide (SiC). The catalyst was loaded between two separate sections of SiC such that it was securely positioned in the isothermal zone the isothermal zone of the reactor. A 60 wt % $C_{16}$/40 wt % $C_{18}$ LAO feed (a blend of Linealene™ 1-Hexadecene and Linealene™ 1-Octadecene, both available from Idemitsu Kosan Co, Ltd.) containing ~8 wt % BO (as determined by GC) was then introduced into the reactor at a WHSV of 10 h$^{-1}$. The isomerization reaction was conducted at a temperature of 150° C. and a pressure of 20 psig (239 kPa-a) for a total of 330 hours. The composition and properties of the resulting product are summarized in Table 3.

TABLE 3

| Property | Units | Test Method | Ex. 12 |
|---|---|---|---|
| $C_{14}$ | wt % | GC | <1.0 |
| $C_{16}$ | wt % | GC | 55.0 |
| $C_{18}$ | wt % | GC | 39.0 |
| $C_{20+}$ | wt % | GC | 6.0 |
| LIO Content | wt % | GC | 76.8 |
| LAO Content | wt % | GC | 3.2 |
| BO Content | wt % | GC | 20 |
| KV at 0° C. | cSt | ASTM D445 | 8.3 |
| KV at 40° C. | cSt | ASTM D445 | 3.5 |
| KV at 100° C. | cSt | ASTM D445 | 1.5 |
| Flash Point | ° C. | ASTM D93 | 143.5 |
| Pour Point | ° C. | ASTM D5950 | −18 |
| Specific Gravity at 15.6/15.6° C. | g/mL | ASTM 4052 | 0.792 |
| Color | Saybolt | ASTM D6045 | +28 |
| Water | wt % | ASTM E203 | 0.005 |
| Anaerobic Biodeg., BRR | — | ISO 11734 | Pass |
| Sediment Toxicity, STR | — | ASTM E1367 | Pass |

Example 13: Isomerization of $C_{16}/C_{18}$ (60:40) LAO Feed in a Fixed Bed Reactor The isomerization test was carried out in a continuous, isothermal, tubular fixed bed reactor. The formulated catalyst prepared in Example 7 (Catalyst D) was loaded into the reactor (1.2 g) between two separate sections of silicon carbide (SiC) such that it was securely positioned in the isothermal zone of the reactor. A 60 wt % $C_{16}$/40 wt % $C_{18}$ LAO feed (a blend of Linealene™ 1-hexadecene and Linealene™ 1-Octadecene, both available from Idemitsu Kosan Co., Ltd.) containing ~7 wt % BO (as determined by GC) was then introduced into the reactor at a WHSV of 10 h$^{-1}$. The isomerization reaction was conducted at a temperature of 135-140° C. and a pressure of 20 psig (239 kPa-a).

Figure 3:
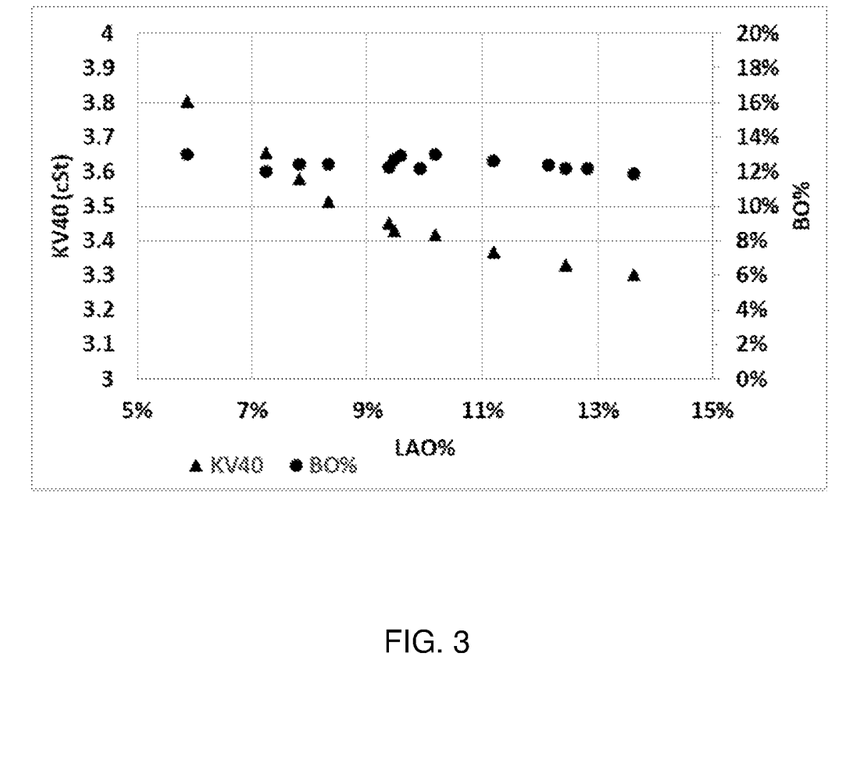
FIG. 3 depicts the KV40 and branched olefin concentrations as a function of the LAO conversion (expressed here as the remaining amount of LAO in wt %) produced in the isomerization reaction conducted in Example 13.

FIG. 3 shows the KV40 and branched olefin concentrations (BO %) of the isomerization mixture as a function of the LAO conversion (expressed here as the remaining amount of LAO in wt %). This figure shows that, with an increased LAO content (or lower conversion), the BO content was approximately constant (about 12-13 wt %) so the LIO+LAO content was approximately constant while the KV40 of the isomerization mixture decreased. Without being bound by any theory, it can be deducted from those results that the KV40 of LAO is lower than the KV40 of LIO and that the KV40 of the isomerization mixture decreases because of the inherent lower KV40 o LAO vs. LIO for a given carbon number, and not because the total linear content (LIO+LAO) in the isomerization mixture increases.

Example 14: Isomerization of $C_{16}/C_{18}$ (60:40) LAO Feed in a Fixed Bed Reactor The isomerization test was carried out in a continuous, isothermal, tubular fixed bed reactor. The formulated catalyst prepared in Example 7 (Catalyst D) was loaded into the reactor (1.2 g) between two separate sections of silicon carbide (SiC) such that it was securely positioned in the isothermal zone of the reactor. A 60 wt % $C_{16}$/40 wt % $C_{18}$ LAO feed (a blend of Linealene™ 1-hexadecene and Linealene™ 1-Octadecene, both available from Idemitsu Kosan Co., Ltd.) containing ~7 wt % BO (as determined by GC) was then introduced into the reactor at a WHSV of 10 h$^{-1}$. The isomerization reaction was conducted at a temperature of 135° C. and a pressure of 20 psig (239 kPa-a) for a total of 1200 hours. No change to the run conditions were made during the run and the catalyst activity was allowed to degrade naturally.

Figure 4:
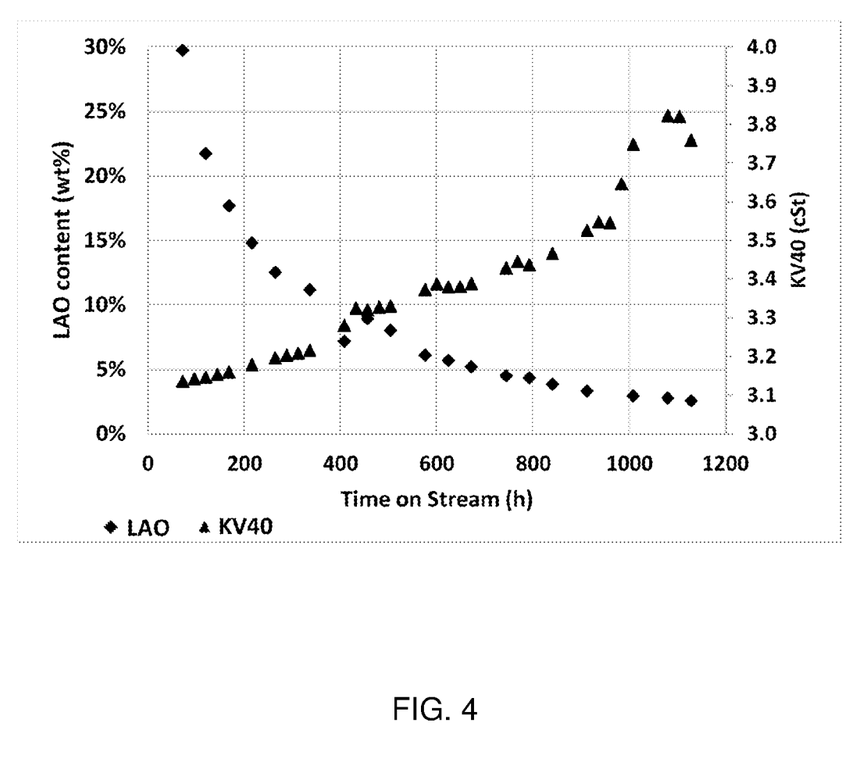
FIG. 4 depicts the KV40 and linear alpha olefin concentrations of the isomerization mixture against time on stream (TOS) produced in the isomerization reactions conducted in Example 14.

FIG. 4 shows the KV40 and the LAO concentrations of the isomerization mixture as a function of the time on stream (TOS). In particular, it shows a decrease of LAO conversion with time on stream due to the deactivation of the catalyst (which results in an increasing LAO content) as well as a clear correlation between decreased LAO conversion and decreased KV40 values. This confirms that the KV40 of the isomerization mixture can be tailored by tuning the LAO conversion.

Example 15: Isomerization of $C_{16}/C_{18}$ (60:40) LAO Feed in a Fixed Bed Reactor The isomerization test was carried out in a continuous, isothermal, tubular fixed bed reactor. The formulated catalyst prepared in Example 7 (Catalyst D) was loaded into the reactor (20 g) between two separate sections of silicon carbide (SiC) such that it was securely positioned in the isothermal zone of the reactor. A 60 wt % $C_{16}$/40 wt % $C_{18}$ LAO feed (a blend of Linealene™ 1-hexadecene and Linealene™ 1-Octadecene, both available from Idemitsu Kosan Co., Ltd.) containing ~7 wt % BO (as determined by GC) was then introduced into the reactor at a WHSV of 10 $h^{-1}$. The isomerization reaction was conducted over a range of temperature between 135 and 150° C. and at a pressure of 20 psig (239 kPa-a). The temperature of the run was adjusted to accommodate catalyst activity loss and to maintain an overall LAO content of less than 10 wt % (i.e. a LAO conversion of at least 90%).

Figure 5:
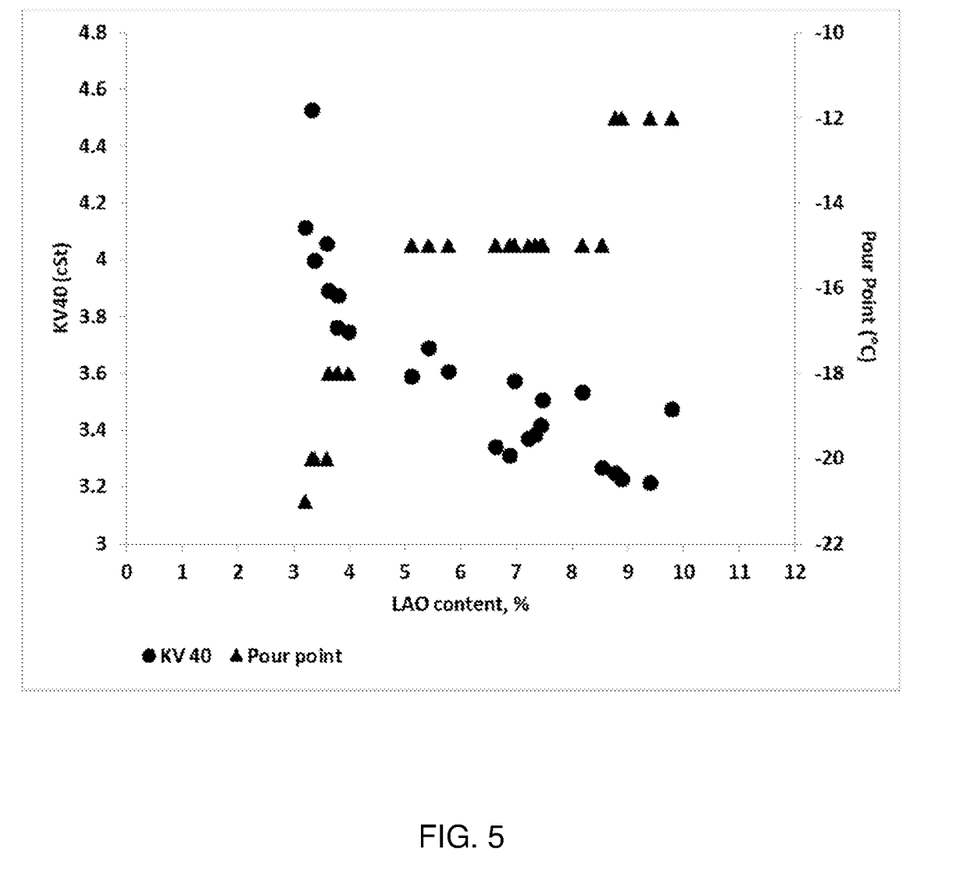
FIG. 5 depicts the KV40 and pour point temperature of product stream sampled at various stages of the reaction run as a function of LAO content in the sample.

FIG. 5 shows the KV40 and pour point temperature of product stream sampled at various stages of the reaction run as a function of LAO content in the sample. As in example 14, the results confirm that the KV40 of the isomerization mixture can be tailored by tuning the LAO conversion. Also, these results show that the isomerization mixtures have a very low pour point of less than −10° C., such as −12° C., −15° C., −18° C., −20° C. or even −21° C.

Figure 6:
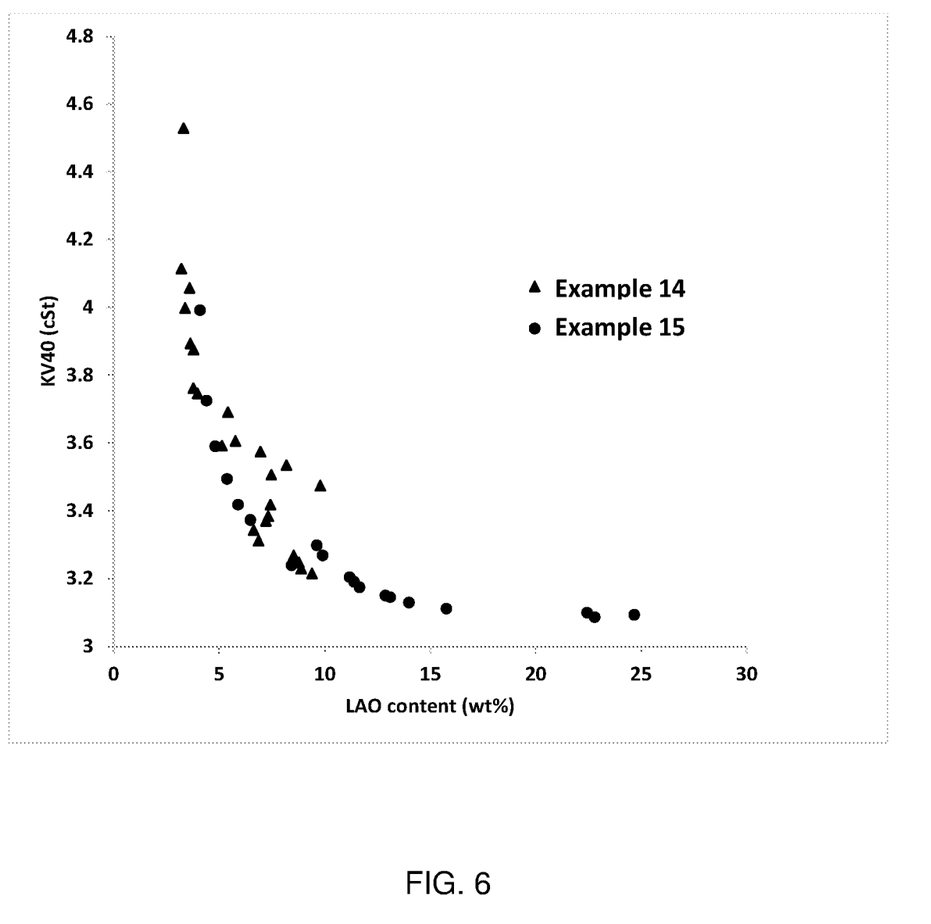
FIG. 6 depicts the KV40 as a function of the LAO content for the data of Examples 14 and 15.

FIG. 6 shows the KV40 as a function of the LAO content for the data of Examples 14 and 15. These results confirm the consistency in correlation between KV40 and LAO content despite the differences in the run conditions.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise whenever a composition, an element or a group of elements is preceded with the transitional phrase "comprising", it is understood that it is also contemplated that the same composition or group of elements with transitional phrases "consisting essentially of," "consisting of", "selected from the group consisting of," or "is" preceding the recitation of the composition, element, or elements and vice versa.

Additionally or alternately, embodiments disclosed herein relate to:

Embodiment 1

A process for isomerizing one or more $C_{14}$-$C_{24}$ alpha olefins to produce an isomerization mixture comprising one or more $C_{14}$-$C_{24}$ internal olefins, the process comprising contacting an olefinic feed comprising the one or more $C_{14}$-$C_{24}$ alpha olefins with a catalyst under isomerization conditions, wherein the catalyst comprises a molecular sieve having an MWW framework.

Embodiment 2

The process of embodiment 1, wherein the molecular sieve is of the MCM-22 family, preferably wherein the molecular sieve is selected from the group consisting of MCM-22, MCM-49 and MCM-56, in particular from MCM-22 and MCM-49, more particularly MCM-22.

Embodiment 3

The process of embodiment 1 or 2, wherein the molecular sieve has a $SiO_2/Al_2O_3$ molar ratio within the range from about 10 to about 50, preferably from about 20 to about 40.

Embodiment 4

The process of any one of embodiments 1 to 3, wherein the catalyst further comprises a binder selected from clay, inorganic oxides, and mixtures or combinations thereof, in particular in an amount of from about 20 wt % to about 50 wt % based on the weight of the isomerization catalyst.

Embodiment 5

The process of embodiment 4, wherein the binder comprises silica and/or alumina.

Embodiment 6

The process of any one of embodiments 1 to 5, wherein the olefinic feed has an average carbon number of greater than or equal to 14, preferably from 14 to 24, more preferably from 14 to 20, most preferably from 16 to 18, in particular wherein the olefinic feed consists essentially of $C_{16}$-$C_{18}$ alpha olefins, such as a $C_{16}/C_{18}$ linear alpha olefin mixture.

Embodiment 7

The process of any one of embodiments 1 to 6, further comprising passing the olefinic feed through a guard bed prior to contacting with the catalyst, preferably wherein the guard bed contains a molecular sieve.

Embodiment 8

The process of any one of embodiments 1 to 7, wherein the olefinic feed comprises $C_{16}$ alpha olefins at a concentration of at least about 40 wt % based on the total weight of the olefinic feed.

Embodiment 9

The process of embodiment 8, wherein the olefinic feed comprises $C_{16}$ alpha olefins at a concentration of at least about 60 wt %, such as at least about 65 wt % based on the total weight of the olefinic feed, and wherein the olefinic feed comprises $C_{18}$ alpha olefins at a concentration of at most about 40 wt %, such as at most about 35 wt % based on the total weight of the olefinic feed.

Embodiment 10

The process of any one of embodiments 1 to 9, wherein the isomerization conditions comprise a temperature from about 50° C. to about 200° C.

Embodiment 11

The process of embodiment 10, wherein the temperature ranges from about 100° C. to about 180° C., particularly from about 110° C. to about 170° C., more particularly from about 130° C. to about 150° C.

Embodiment 12

The process of any one of embodiments 1 to 11, wherein the olefin feed is supplied at a weight hourly space velocity (WHSV) from about 1 h$^{-1}$ to about 50 h$^{-1}$, preferably from about 2 h$^{-1}$ to about 20 h$^{-1}$

Embodiment 13

The process of any one of embodiments 1 to 12, wherein the rate of conversion of the $C_{14}$-$C_{24}$ alpha olefins to the $C_{14}$-$C_{24}$ internal olefins is at least about 40%.

Embodiment 14

The process of embodiment 13, wherein the rate of conversion of the $C_{14}$-$C_{24}$ alpha olefins to the $C_{14}$-$C_{24}$ internal olefins is at least about 71%, such as at least about 75%.

Embodiment 15

The process of embodiment 13, wherein the rate of conversion of the $C_{14}$-$C_{24}$ alpha olefins to the $C_{14}$-$C_{24}$ internal olefins is from about 71% about 90%.

Embodiment 16

The process of embodiment 13, wherein the rate of conversion of the $C_{14}$-$C_{24}$ alpha olefins to the $C_{14}$-$C_{24}$ internal olefins is more than about 90%.

Embodiment 17

The process of any one of embodiments 1 to 16, wherein the isomerization mixture comprises linear internal olefins at a concentration of about 40 wt % or more, in particular of about 55 wt % or more or of about 60 wt % or more based on the total weight of the isomerization mixture.

Embodiment 18

The process of any one of embodiments 1 to 16, wherein the isomerization mixture comprises linear internal olefins at a concentration of about 60 wt % or more, in particular of about 70 wt % or more or of about 80 wt % or more, based on the total weight of the isomerization mixture.

Embodiment 19

The process of any one of embodiments 1 to 18, wherein the isomerization mixture comprises branched olefins at a concentration of about 35 wt % or less, such from 0 wt % to about 35 wt % or from 0 wt % to about 30 wt % based on the total weight of the isomerization mixture.

Embodiment 20

The process of any one of embodiments 1 to 19, wherein the isomerization mixture comprises branched olefins at a concentration ranging from about 5 wt % to about 35 wt %, in particular from about 5 wt % to about 30 wt %, or from about 10 wt % to about 30 wt %, or from about 10 wt % to about 25 wt %, based on the total weight of the isomerization mixture.

Embodiment 21

The process of any one of embodiments 1 to 20, wherein the isomerization mixture comprises linear alpha olefins at a concentration of less than about 35 wt % based on the total weight of the isomerization mixture.

Embodiment 22

The process of embodiment 21, wherein the isomerization mixture comprises linear alpha olefins at a concentration of less than about 10 wt %, preferably less than about 5 wt %, based on the total weight of the isomerization mixture.

Embodiment 23

The process of embodiment 21, wherein the isomerization mixture comprises linear alpha olefins at a concentration of from about 10 wt % to about 29 wt %, preferably from about 10 wt % to about 20 wt %, more preferably from about 10 wt % to 15 wt %, based on the total weight of the isomerization mixture.

Embodiment 24

The process of any one of embodiments 1 to 23, wherein the isomerization mixture has a pour point of about −6° C. or less, preferably −12° C. or less, more preferably −15° C. or less.

Embodiment 25

A drilling fluid or paper sizing composition comprising the isomerization mixture produced by any one of embodiments 1 to 24.

Embodiment 26

An olefinic mixture comprising about 60 wt % or more of $C_{14}$-$C_{24}$, preferably $C_{16}$-$C_{18}$, linear internal olefins based on the weight of the mixture, from about 0 wt % to about 30 wt % or from about 10 wt % to about 30 wt % of branched olefins based on the weight of the mixture, and less than about 10 wt % of linear alpha olefins based on the weight of the mixture.

Embodiment 27

The olefinic mixture of embodiment 26, wherein the mixture comprises from 0 wt % to about 25 wt % or from about 10 wt % to about 25 wt % of branched olefins based on the weight of the mixture.

Embodiment 28

The olefinic mixture of embodiment 26 or 27, wherein the mixture has a pour point of about −15° C. or less.

Embodiment 29

An olefinic mixture comprising about 41 wt % or more of $C_{14}$-$C_{24}$, preferably $C_{16}$-$C_{18}$, linear internal olefins based on the weight of the mixture, from about 0 wt % to about 30 wt % or from about 10 wt % to about 30 wt % of branched olefins based on the weight of the mixture, and from about 10 wt % to about 29 wt %, preferably from about 10 wt % to about 20 wt %, more preferably from about 10 wt % to about 15 wt %, of linear alpha olefins based on the weight of the mixture.

Embodiment 30

The olefinic mixture of embodiment 29, wherein the mixture comprises from 0 wt % to about 25 wt % or from about 10 wt % to about 25 wt % of branched olefins based on the weight of the mixture.

Embodiment 31

The olefinic mixture of embodiment 29 or 30, wherein the mixture has a pour point of about −6° C. or less, preferably about −10° C. or less.

Embodiment 32

The olefinic mixture of any one of embodiments 26 to 31, wherein the mixture has a KV40 of from about 2.0 cSt to about 5.0 cSt, preferably from about 3.0 cSt to about 4.0 cSt.

Embodiment 33

The olefinic mixture of any one of embodiments 26 or 32, wherein the mixture has a KV100 of from about 1 cSt to about 2 cSt.

The invention claimed is:

1. A process for isomerizing one or more $C_{14}$-$C_{24}$ alpha olefins to produce an isomerization mixture comprising one or more $C_{14}$-$C_{24}$ internal olefins, the process comprising contacting an olefinic feed comprising the one or more $C_{14}$-$C_{24}$ alpha olefins with a catalyst under isomerization conditions, wherein the catalyst comprises a molecular sieve having an MWW framework, and wherein the olefin feed is supplied at a weight hourly space velocity (WHSV) from 2 $h^{-1}$ to 50 $h^{-1}$.

2. The process of claim 1, wherein the molecular sieve is of the MCM-22 family.

3. The process of claim 1, wherein the molecular sieve has a $SiO_2/Al_2O_3$ molar ratio within the range from 10 to 50.

4. The process of claim 1, wherein the catalyst further comprises a binder selected from clay, inorganic oxides, and mixtures or combinations thereof.

5. The process of claim 4, wherein the binder comprises silica and/or alumina.

6. The process of claim 1, wherein the olefinic feed has an average carbon number of greater than or equal to 14.

7. The process of claim 1, further comprising passing the olefinic feed through a guard bed prior to contacting with the catalyst.

8. The process of claim 1, wherein the olefinic feed comprises $C_{16}$ alpha olefins at a concentration of at least 40 wt % based on the total weight of the olefinic feed.

9. The process of claim 8, wherein the olefinic feed comprises $C_{16}$ alpha olefins at a concentration of at least 65 wt % based on the total weight of the olefinic feed, and wherein the olefinic feed comprises $C_{18}$ alpha olefins at a concentration of at most 40 wt %, based on the total weight of the olefinic feed.

10. The process of claim 1, wherein the isomerization conditions comprise a temperature from 50° C. to 200° C.

11. The process of claim 1, wherein the rate of conversion of the $C_{14}$-$C_{24}$ alpha olefins to the $C_{14}$-$C_{24}$ internal olefins is from 71% to 90%.

12. The process of claim 11, wherein the rate of conversion of the $C_{14}$-$C_{24}$ alpha olefins to the $C_{14}$-$C_{24}$ internal olefins is more than 90%.

13. The process of claim 1, wherein the isomerization mixture comprises linear internal olefins at a concentration of 40 wt % or more based on the total weight of the isomerization mixture.

14. The process of claim 1, wherein the isomerization mixture comprises branched olefins at a concentration of 35 wt % or less based on the total weight of the isomerization mixture, based on the total weight of the isomerization mixture.

15. The process of claim 1, wherein the isomerization mixture comprises linear alpha olefins at a concentration of less than 35 wt % based on the total weight of the isomerization mixture.

16. The process of claim 1, wherein the isomerization mixture has a pour point of −6° C. or less.

17. A drilling fluid or paper sizing composition comprising the isomerization mixture produced by claim 1.

* * * * *